United States Patent [19]

Marut

[11] Patent Number: 4,738,661
[45] Date of Patent: Apr. 19, 1988

[54] GASTROSTOMY BELT

[76] Inventor: Marie R. Marut, 10 Pineybranch Rd., Cranbury, N.J. 08512

[21] Appl. No.: 908,640

[22] Filed: Sep. 18, 1986

[51] Int. Cl.$^4$ .............................................. A61M 5/32
[52] U.S. Cl. .................... 604/179; 604/333; 604/345; 128/DIG. 26; 2/DIG. 7
[58] Field of Search ............... 604/332, 333, 337, 345, 604/174, 179, 180; 128/100, 101, 106, 114, 132 R, 133, DIG. 15, DIG. 26; 224/148, 163, 224, 227–229; 2/DIG. 7, 311, 312, 317, 338; D2/627–630; D3/106

[56] References Cited

U.S. PATENT DOCUMENTS

| | | | |
|---|---|---|---|
| 2,087,620 | 7/1937 | Lipton | 2/311 |
| 2,612,895 | 10/1952 | Magee | 604/345 |
| 3,125,093 | 3/1964 | Hutchins | 604/332 |
| 3,648,703 | 3/1972 | Manker | 128/DIG. 26 |
| 3,804,091 | 4/1974 | Nolan et al. | 604/333 |
| 4,221,215 | 9/1980 | Mandelbaum | 128/DIG. 26 |
| 4,578,062 | 3/1986 | Scheider | 128/DIG. 26 |
| 4,596,560 | 6/1986 | Simpson | 604/337 |
| 4,666,432 | 5/1987 | McNeish et al. | 604/345 |

FOREIGN PATENT DOCUMENTS

| | | | |
|---|---|---|---|
| 574258 | 4/1959 | Canada | 604/345 |
| 695369 | 8/1953 | United Kingdom | 604/345 |

*Primary Examiner*—Dalton L. Truluck
*Assistant Examiner*—Mario Costantino
*Attorney, Agent, or Firm*—Sachs & Sachs

[57] ABSTRACT

A belt for use on patients having had a gastrostomy surgical procedure perfomed wherein a flexible entrance tube extends outwardly, via a stoma, from the patient's body. The belt includes a pocket into which extends the flexible tube so that any excretions emanating therefrom will be absorbed by the absorbent material of the pocket and may include anti-bacterial medicaments and/or odor neutralizing medicaments therein, fits comfortably around the patient's body and may be reused many times without deteriation.

12 Claims, 2 Drawing Sheets

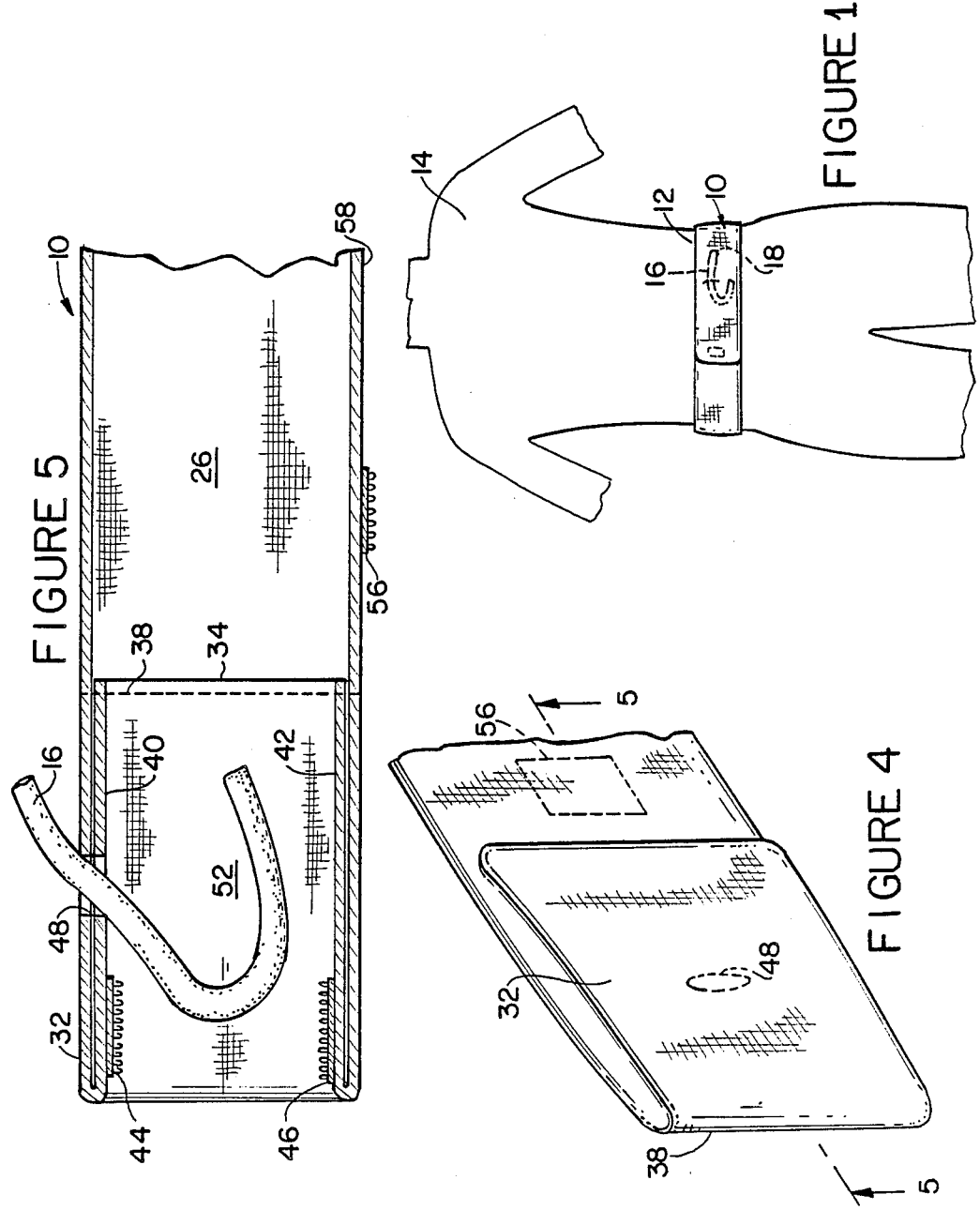

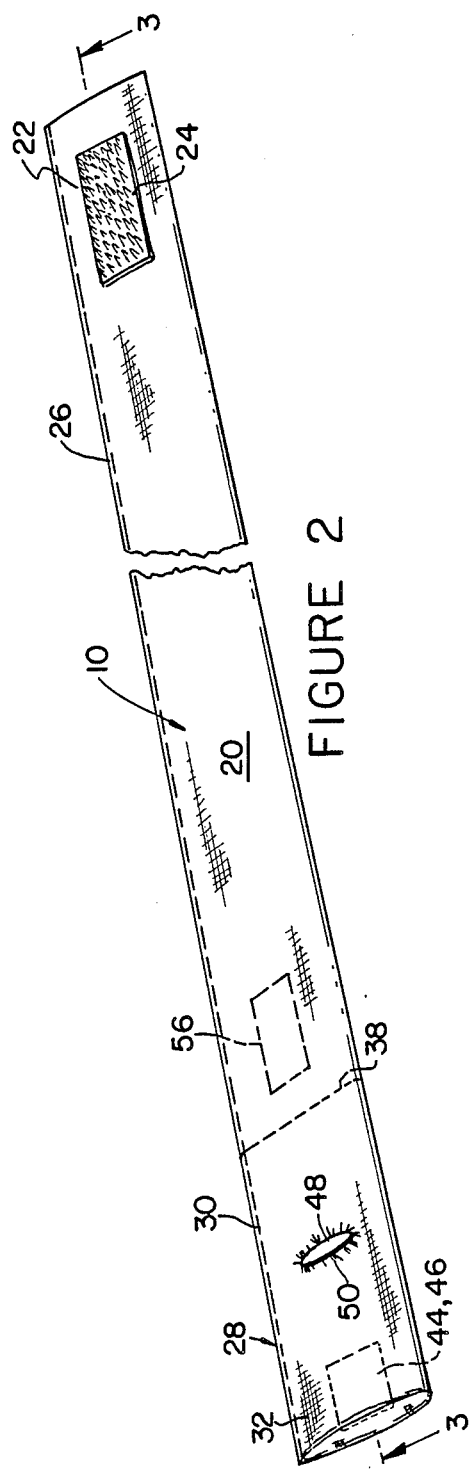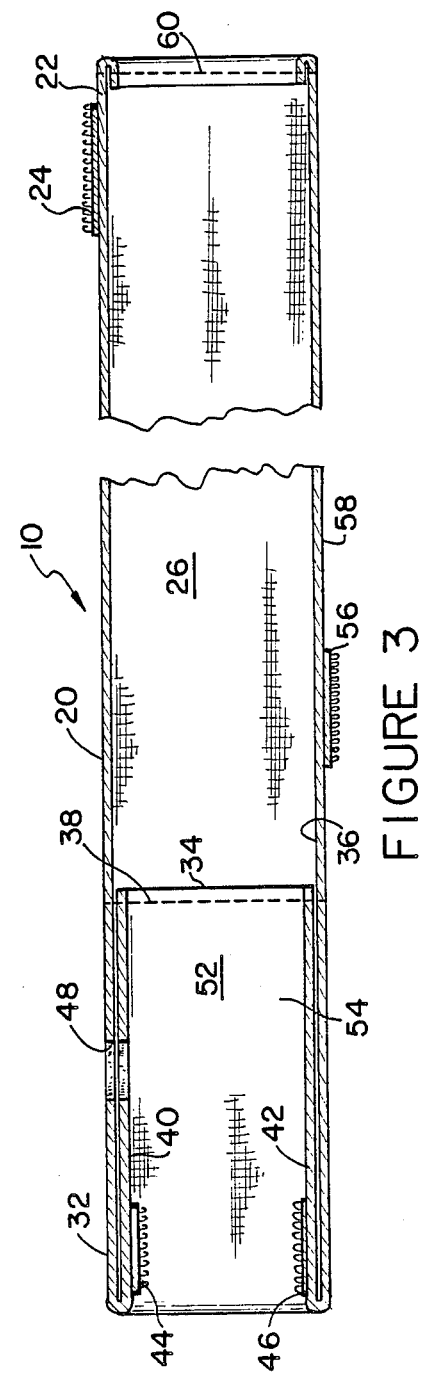

GASTROSTOMY BELT

BACKGROUND OF THE INVENTION

1. Field of the Invention

The present invention relates generally to medical appliances and more specifically to a belt for use on patients that have had a gastrostomy surgical procedure performed on them.

2. Background of the Invention

The art abounds with many surgical drains, belts and appliances in order to make a patient more comfortable after having undergone a surgical procedure of one type or the other. In particular, many appliances have been designed for use on patients having gone through an ostomy procedure such as U.S. Pat. No. 4,533,355 issued to Marjorie A. Fair on Aug. 6, 1985 relating to a loose-fitting garment generally in the shape of loose-fitting shorts or panties. Another belt device is disclosed in U.S. Pat. No. 3,773,048 issued to Alexander J. Kirkliauskas on Nov. 20, 1973 which relates to a medical appliance or belt disposed at a particular position on the body and includes a panel of absorbent, non-allergic material and an opening for receiving a medical appliance. This device has been specifically designed for use on patients who have had this type of surgery performed thereon.

Many of the types of devices and appliances are available for use on patients that require some means for capturing excretions or other bodily fluids that exit the body, via a stoma. However, there is little if any devices made available for use on patients having had a gastrostomy procedure performed thereon where the entrance of feeding materials into the stomach is of primary concern and excretions exiting therefrom are minimal or non-existent.

Therefore, it is an object of the present invention to provide an inexpensive, reuseable belt, comfortable for a patient to wear and does not provide any obtrusive portions which can be detectable when worn together with conventional outer garments.

It is another object of the present invention to provide a readily adjustable belt for use on patients having had a gastrostomy surgical procedure performed thereon wherein the outwardly extending tubular member through which food is presented may be maintained in a generally clean atmosphere (pocket) which may include medicaments to prevent the growth of bacteria and/or neutralize any odors occurring from small drippings that may occur.

It is yet another object of the present invention to provide an easily changeable belt for use on patients having had a gastrostomy procedure performed thereon which may be washed many times and is reuseable.

It is a further object of the present invention to provide an inexpensive disposable gastrostomy belt which is comfortable to wear.

It is still yet another object of the present invention to provide a belt that may be utilized long after the gastrostomy wound is completely healed.

It is yet a further object of the present invention to provide an inexpensive disposable belt which may be reused or disposed of and may be readily exchanged by a person having had a gastrostomy procedure performed thereon.

Further objects and advantages of the instant invention will come to mind by those knowledgeable in the art having seen the disclosure.

SUMMARY OF THE INVENTION

A belt for use on a patient having been subjected to a gastrostomy surgical procedure, according to the principle of the present invention, wherein a flexible entrance tube extends outwardly, via a stoma, from the patient's body, comprises an elongated tubular material member of sufficient length to circumscribe the torso of the patient. One end portion of the elongated tubular member is provided with a first attaching device disposed on the inner surface proximate the distal edge of the one end portion and extends inwardly towards the other end portion of the tubular member. The other end portion of the tubular member includes first cooperating attaching device disposed on the outer surface remote from the other distal edge of the other end portion. A portion of the tubular member is folded inwardly within itself providing at least four layers of material. The inner surface of the material proximate the other distal edge is provided with second attaching and cooperating devices for closing the other distal end. The inwardly extending edge of the other distal end being provided with a fold line extending through all of the layers of material. The fold line is disposed between the first cooperating attaching device and the other distal edge. An opening is disposed in the other end portion between the fold line and the other distal edge and extends only through two layers of material and is adapted to receive the outwardly extending flexible tube provided on the patient.

The foregoing and other objects and advantages will appear from the description to follow. In the description reference is made to the accompanying drawing which forms a part hereof, and which is shown by way of illustration a specific embodiment in which the invention may be practiced. This embodiment will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

In order that the invention may be more fully understood, it will now be described, by way of example, with reference to the accompanying drawing in which:

FIG. 1 is a pictorial representation of the gastrostomy belt worn on a patient, according to the principles of the present invention.

FIG. 2 is a pictorial representation of the gastrostomy belt open and extended;

FIG. 3 is a cross-sectional view of the belt taken along 3—3 of FIG. 2;

FIG. 4 is a pictorial representation of one end of the gastrostomy belt showing it in its closed position; and FIG. 5 is a cross-sectional view taken along 5—5 of FIG. 4 with the addition of the outwardly extending tubular member disposed in the opening provided therein.

DESCRIPTION OF THE PREFERRED EMBODIMENT

Referring now to the figures and in particular, to FIGS. 1, 2, 3 and 5 there is shown a gastrostomy belt 10 according to the principles of the present invention, disposed around the waistline 12 of a patient 14. Emanating from the general waistline area is a flexible tubular member 16 extending through the abdominal wall and through a stoma 18 provided in the skin of the patient 12 providing direct access to the stomach, not shown, of the patient.

FIG. 2 discloses the gastrostomy belt 10 in its open or extended position with the inwardly facing surface 20 facing the viewer. The end portion 22 has sewn thereon a conventional hook-shaped material pad 24 more commonly known as VELCRO. The pad 24 is sewn around its periphery onto the tubular material used to fabricate the body 26 of the belt 10, which is preferably fabricated from a cotton velour material that is either tubular in shape of fabricated from an elongated rectangular material which is folded upon itself and sewn along the edge 28 by stitches 30 disposed inwardly therefrom, in a conventional manner.

The other end 32 of the tubular body member 26 is folded inwardly upon itself with its edge 34 disposed within the opening 36 of the body 26. Slightly removed from the edge 34 a line of stitching 38 is provided to fasten the edge 34 in position. The stitching 38 provides a fold line, since it pierces all four layers of material.

The inner surfaces 40 and 42 of the body member 26 are also provided with a hooked-shaped material pad 44 on one of the inner surfaces and a eyelet shaped pad 46 on the other inner surface. The first inner surface 40 when pressed against the other surface 42 seals the end 32 thus, providing a closed pocket thereby. An elongated opened 46 extending transverse to the longitudinal axis of the body member 26 extends through only two layers of material and may be reinforced with conventional button hole stitching 48 around the opening. The pocket 52 formed by closing the end 32 (allowing the hooked material pad 44 to contact the looped material pad 46) may be provided with a medicament 54 which retards, destroys or prevents bacterial growth and/or odors, the need for which will be disclosed hereinafter.

An additional looped pad 56 is sewn to the outwardly extending surface 58 of the body 26 which is positioned to cooperate with hooked pad 24 when circumscribing the torso of a patient 14. End 22 may also be folded upon itself and stitched permanently closed by stitches 60, in a conventional manner.

In operation, the flexible tubular member 16 extending, via the stoma 18 provided in the patient 12 will be utilized for feeding nutrients directly into the stomach of the patient and when the feeding is completed, the tube 16 is wiped off and folded upon itself or clamped by a clamp, not shown, and then inserted, via the opening 48 provided in the body member 26 of belt 10. The pocket 52 provided at end 32 of belt 10 may be filled with an anti-bacterial medicament which prohibits bacterial growth and/or medicaments which will remove any odor occurring from small amounts of seepage or dripping that may flow backwardly, via tube 16 into pocket 52, thus, preventing the formation of odor or bacteria growth. Once the tube 16 is clamped off and inserted within opening 48, extending into pocket 52, end 32 is folded back upon itself along the fold line provided by the stitching 38. The belt 10 is then wrapped around the waistline of the patient so that the hooked shaped material pad 24 can come into contact with the looped material pad 56, thereby holding the belt to the waistline of the patient. The pads of course, are elongated and may be made to extend over a fairly large distance so that they may accommodate patients having waistlines of different sizes.

Hereinbefore has been disclosed an inexpensive, reuseable, disposable gastrostomy belt which is comfortable to wear and serves a long felt need. It will be understood that various changes in the details, materials, arrangements of parts and operating conditions which have been herein described and illustrated in order to explain the nature of the invention may be made by those skilled in the art within the principles and scope of the instant invention.

Having thus set forth the nature of the invention, what is claimed is:

1. A belt for use on a patient having been subjected to a gastrostomy surgical procedure wherein a flexible entrance tube means extends outwardly, via a stoma from the patient's body, comprising:
   an elongated tubular member having an inner surface and an outer surface and being of sufficient length to circumscribe the torso of said patient and including a first end portion and a second end portion;
   (i) said first end portion of said elongated tubular member being provided with first attaching means disposed on the inner surface proximate the distal edge of said one end portion and extending towards said second end portion of said tubular member,
   (ii) said second end portion of said tubular member including;
      (a) first cooperating attaching means disposed on said outer surface remote from the distal edge of said second end portion, for cooperating with said first attaching means,
      (b) a portion of said tubular member folded inwardly within itself providing at least four layers of said material, the inner surface of said material proximate said second distal edge being provided with second attaching means and cooperating means for closing said second distal edge,
      (c) the inwardly extending edge of said second end portion being provided with a fold line extending through all said layers of material, said fold line being disposed between said first cooperating attaching means and said second distal edge,
      (d) opening means disposed in said second end portion between said fold line and said second distal edge extending through only two layers of material for receiving said outwardly extending flexible tube means.

2. A gastrostomy belt according to claim 1 wherein said elongated tubular member is fabricated from a soft, washable, durable, material capable of being washed many times.

3. A gastrostomy belt according to claims 1 or 2 wherein said fold line is provided by stitching through all said four layers of material.

4. A gastrostomy belt according to claim 1 wherein said opening means is elongated and extends perpendicular to the longitudinal axis of said elongated tubular member.

5. A gastrostomy belt according to claim 4 wherein said elongated opening means is provided with edge reinforcement.

6. A gastrostomy belt according to claim 5 wherein said edge reinforcement comprises button-hole stitches.

7. A gastrostomy belt according to claims 1 or 2, wherein said first and second attaching means includes a plurality of relatively stiff hooked shaped fibers and said first and second cooperating attaching means includes relatively soft loop-shaped fibers, said first and second attaching means and said first and second cooperating attaching means being sewn to said elongated tubular member.

8. A gastrostomy belt according to claim 2 wherein said elongated tubular member is sewn on said the edge of said one end portion.

9. A gastrostomy belt according to claims 1 or 2 wherein said other end portion contains medicaments therein.

10. A gastrostomy belt according to claim 9 wherein said medicaments are odor neutralizing.

11. A gastrostomy belt according to claim 9 wherein said medicaments are anti-bacterial.

12. A belt for use on a patient having been subjected to a gastrostomy surgical procedure wherein a flexible entrance tube means extends outwardly, via a stoma from the patient's body, comprising:

an elongated tubular member having a first end, a second end, an inner side for facing said patient's body and an outer side which faces away from said patient's body;
(i) said first end being provided with first attaching means disposed on said inner side proximate the distal edge of said first end and extending towards said second end,
(ii) said second end being folded inwardly within itself along part of its length to form a pocket position which is four layers of material thick, having an opening, the second end of said tubular member defining a fold line disposed between said first and second ends,
    (a) first cooperating attaching means disposed on said outer side between said fold line and said first end for cooperating with said first attaching means,
    (b) second attaching means and second cooperating means for cooperating with said second attaching means being disposed within said pocket portion to close said opening of said pocket portion;
    (c) opening means disposed in said pocket portion between said fold line and said opening extending through only two layers of material on said inner side for receiving said outwardly extending flexible tube means.

* * * * *